United States Patent [19]

Hatch

[11] Patent Number: 4,621,153

[45] Date of Patent: Nov. 4, 1986

[54] PURIFICATION AND RECOVERY OF AMINO ACIDS

[75] Inventor: Randolph T. Hatch, Wellesley, Mass.

[73] Assignee: Biotechnica International, Inc., Cambridge, Mass.

[21] Appl. No.: 706,041

[22] Filed: Feb. 27, 1985

[51] Int. Cl.[4] ............................................. C07C 99/12
[52] U.S. Cl. .................................................. 562/443
[58] Field of Search ....................... 562/445, 443, 444

[56] References Cited

U.S. PATENT DOCUMENTS

| | | | |
|---|---|---|---|
| 3,159,632 | 12/1964 | Sargent | 562/443 |
| 3,904,585 | 9/1975 | Thunberg | 562/443 |
| 4,071,500 | 1/1978 | Cooper et al. | 562/443 |
| 4,167,564 | 9/1979 | Jensen | 562/443 |
| 4,399,304 | 8/1983 | Malsuishi et al. | 562/445 |
| 4,436,910 | 3/1984 | Kleemann et al. | 562/443 |
| 4,446,055 | 5/1984 | Shah et al. | 562/443 |

FOREIGN PATENT DOCUMENTS

| | | | |
|---|---|---|---|
| 2917603 | 11/1980 | Fed. Rep. of Germany | 562/445 |
| 4423516 | 10/1969 | Japan | 562/443 |
| 56-57750 | 5/1981 | Japan | 562/445 |
| 56-57749 | 5/1981 | Japan | 562/445 |
| 59-39857 | 3/1984 | Japan | 562/443 |
| 1019574 | 2/1966 | United Kingdom | 562/445 |

OTHER PUBLICATIONS

Rudnick, Chem. Abst., vol. 92, #71323t (1980).
Hardel, Chem. Abst., vol. 66, #32420r (1967).
Chem. Abstracts (1980) 93:716, para. 93:168613w.
Yamada et al. (1981) Applied and Environmental Microbiology 42(5):773–778.
Sakamoto et al., Chem. Abstracts (1979) 91:1773363c.
Tsau, Chem. Abstracts 99:13458f.

Primary Examiner—James H. Reamer

[57] ABSTRACT

A method of recovering an amino acid from a mixture by providing a source of bivalent metal ions capable of forming a complex with the amino acid, the complex being insoluble at least in a particular pH range. The complex is separated from the mixture and then dissociated, the metal ions thereby being removed from the amino acid. The amino acid may be recovered continuously from a fermentation broth of microorganisms.

13 Claims, 2 Drawing Figures

4,621,153

PURIFICATION AND RECOVERY OF AMINO ACIDS

BACKGROUND OF THE INVENTION

This invention relates to purification and recovery of amino acids from mixtures containing undesired impurities, for example, fermentation broths used in the microbial production of amino acids. As used in this application, the term amino acid means one of the naturally occurring amino carboxylic acids of which proteins are comprised.

Desired amino acids present at very low concentrations in complex mixtures often must be purified and recovered before they can be used. In particular, amino acids produced by a microorganism usually must be recovered from a fermentation broth containing nutrients, other amino acids, small peptides, other small organic compounds, and various larger components including cell debris, enzymes, and other proteins. Amino acids produced by chemical synthesis also must be recovered from a reaction medium containing raw materials and by-products.

Various methods of amino acid recovery have been disclosed. One specific method involves an ion exchange resin, often an anion exchange resin in a column, which binds the amino acid under certain conditions to separate it from the reaction mixture, and then releases the amino acid under other conditions to permit recovery of a crude solution of the amino acid. See, for example, Chem. Abstracts (1980) 93: 716, para. 93: 168613w; Yamada et al. (1981) Applied and Environmental Microbiology 42(5): 773–778; and Sakamoto et al., Chem. Abstracts (1979) 91: 1773363c.

The crude amino acid solution then may be further purified. For example, Chem. Abstracts (1980), cited above, discloses purifying the crude isolate obtained from the resin by treating the isolate with an organic acid to form a salt with the phenylalanine cation. The salt solution is adjusted to pH 5.48 to precipitate the pure phenylalanine.

Thunberg U.S. Pat. No. 3,904,585 discloses recovering amino acids, specifically alanine and glycine, by boiling to concentrate the solution and cooling to cause precipitation.

SUMMARY OF THE INVENTION

In one aspect, the invention features a method of recovering an amino acid from a mixture by providing a source of bivalent metal ions capable of forming a complex with the amino acid, the complex being insoluble at least in a particular pH range. In describing the structure formed by the amino acid and bivalent metal ion, the term "complex" is meant to include, without limitation, structures that could be termed coordination complexes or salts and that are formed by the association of two stable entities in solution under conditions that do not affect the amino acid's stability. To recover the amino acid, the insoluble complex is removed from the liquid mixture, and then it is dissociated, the metal ions thereby being separated from the amino acid.

In preferred embodiments, the method is used to recover an amino acid from a fermentation broth of microorganisms. The broth is separated into a solid phase and a liquid phase comprising the amino acid. A source of bivalent metal ions is provided in the liquid phase at a pH that causes formation of an insoluble ion/amino acid complex, which is removed from the liquid phase and then dissociated. Also in preferred embodiments, the amino acid is phenylalanine, and the metal ion is calcium. The method is used in a continuous phenylalanine recovery process in which a portion of the fermentation broth is drawn off and separated into liquid and solid phases, the phenylalanine remaining in the liquid phase. The solid phase is returned to the broth. The insoluble calcium ion/phenylalanine complex is formed by raising the pH. After removal of the insoluble complex, the liquid phase also may be returned to the broth after pH adjustment. Filtration is used to separate the solid and liquid phases. Calcium is separated from the complex by forming a soluble salt, e.g., calcium chloride, and precipitating the phenylalanine by concentrating it above its solubility limit, e.g., by evaporation.

The method is particularly advantageous because of the surprisingly low solubility of the complex. The presence of relatively little metal ion will effect separation of amino acids that are present in low concentrations in complex organic mixures. Continuous fermentation is made possible by removing the desired product before it can build to detrimental levels in the fermentation broth. Because the solubility of the complex is pH dependent, the complex can alternately be made soluble to remove it from solids, and then insoluble to remove it from the liquid phase. Product removal is enabled without significantly depleting other components in the fermentation broth by returning most of the broth components (solids, liquids, or both) that have been drawn off for amino acid recovery. In this way, loss of valuable cells and nutrients from the broth is minimized, and disturbance to fermentation conditions is minimized.

Other features and advantages of the invention will be apparent from the following description of the preferred embodiments and from the claims.

DESCRIPTION OF THE PREFERRED EMBODIMENT

I first briefly describe the figures.

Figure 1:
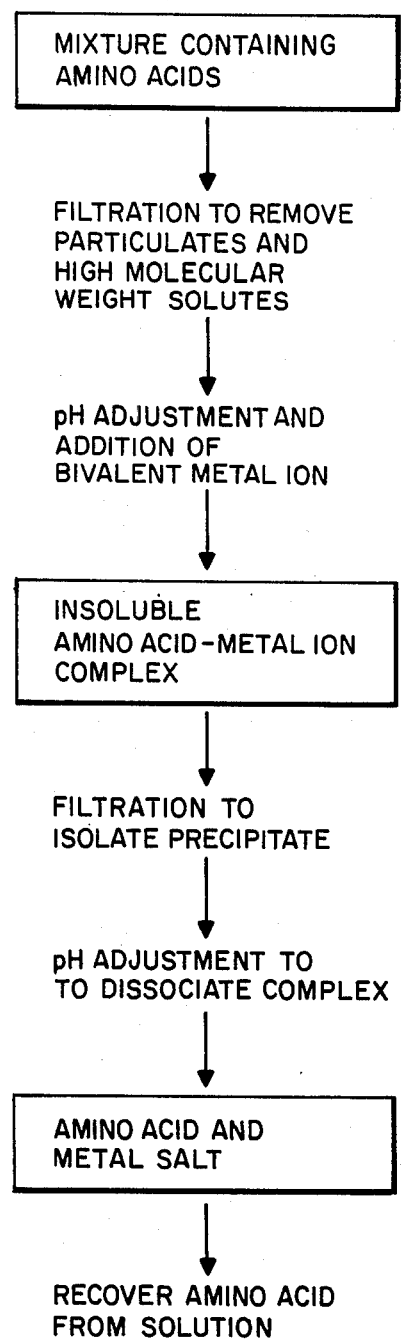
FIG. 1 is a flow diagram for a general amino acid recovery process.

FIG. 1 shows the general steps in a preferred process according to the invention. A mixture containing the desired amino acid in low concentrations is filtered and subjected to pH adjustment, after which a source of bivalent metal ions is added to cause the formation of an insoluble complex with the amino acid. For example, a phenylalanine solution is pH-adjusted with $NH_4OH$ to a pH selected in the range described below to form an insoluble calcium ion complex. $Ca(OH)_2$ is then added to precipitate the phenylalanine complex.

The insoluble complex is isolated by filtration and then the pH is readjusted to effect separation of the complex components. Specifically, an acid is used that will form a soluble salt with the bivalent metal ion.

Figure 2:
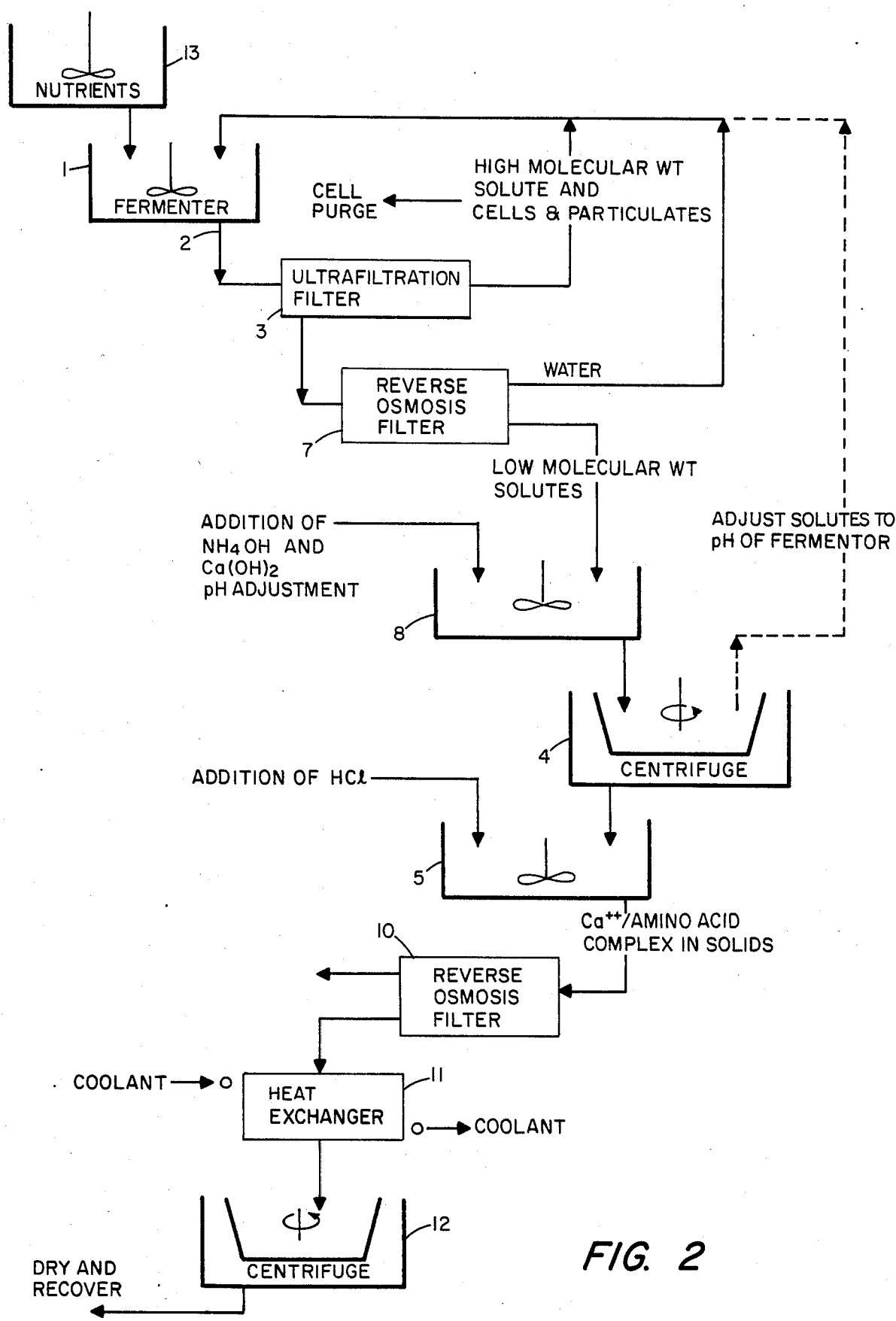
FIG. 2 is a flow diagram for a continuous flow amino acid recovery process.

In FIG. 2, a continuous fermentor 1 is used to culture microorganisms that produce L-phenylalanine so as to establish an extracellular concentration of that compound. Any number of microorganisms and fermentation broths are suitable for this purpose. For example, *E. coli* YMC9 modified as described in U.S. Ser. No. 653,193, filed Sept. 24, 1984 (ATCC No. 39857) may be cultured in a suitable medium. Nutrients are furnished from a nutrient vat 13 as they are needed.

After a suitable fermentation period establishes a sufficient concentration of L-phenylalanine, a valve to line 2 is opened to remove a small stream of fermentation broth. The stream is pumped through an ultrafiltration filter 3 to separate the cell mass and particulates. After purging cells as required to maintain a desired cell population, the solids can be returned to the fermentor or stored in a separate vessel for further processing. An appropriate ultrafiltration filter for this purpose is a 100,000 molecular weight cellulosic membrane. A suitable pressure across the filter is 3.8 bars. A flux of 7.6 gallons/ft$^2$ day is suitable.

The filtrate is passed through a reverse osmosis filter 7, and water is recycled to the fermenter. The filtrate then is pH-adjusted in vat 8 to cause the phenylalanine dissolved therein to form an insoluble complex with calcium. The pH at which the complex begins to precipitate is somewhat over 7.0, depending on the composition of the solution. Preferably the pH is raised to at least 8.5. The pH should be kept low enough (e.g. below 11) to avoid hydrolysis of phenylalanine or other destabilizing reactions; most preferably, the pH should be about 9.2. A preferred method for increasing pH is to add NH$_4$OH and if the considerations described below dictate the addition of Ca$^{++}$, Ca(OH)$_2$ may be used to increase the pH.

As a general rule of thumb, the complex solubility constant (Ksp) at about pH 9 is about $3 \times 10^{-4}$M$^3$, so that a Ca$^{++}$ concentration of 0.5M will reduce the phenylalanine concentration to 0.024M or approximately 4 g/l. Given the Ksp of the Ca$^{++}$-phenylalanine complex, one skilled in the art would be able to provide a suitable concentration of Ca$^{++}$ either by supplementing the nutrient medium with Ca$^{++}$ or, if desired, by adding Ca$^{++}$ to the filtered fermentation broth when adjusting the pH to effect precipitation of the complex. The amount of Ca$^{++}$ used will depend on the phenylalanine concentration in the broth as well as on the desired yield of phenylalanine. I have also found that the solubility of the complex is inversely related to the concentration of NH$_4^+$.

The solution containing the precipitated Ca$^{++}$-phenylalanine complex is centrifuged in centrifuge 4. The liquid phase may be acidified to the pH of the fermentation broth and returned to the fermentor.

The solid precipitate is then acidified with agitation in vat 5 (preferably to a pH between 6.5 and 8.5) to separate the Ca$^{++}$ from the phenylalanine. For example, acidification with HCl yields soluble phenylalanine and soluble CaCl$_2$. The phenylalanine can be crystallized by evaporation of the solvent.

Crystallized phenylalanine is recovered by filtration through reverse osmosis filter 10. The solid phase is passed through heat exchanger 11 to cool it and provide a suitable precipitate to be removed by centrifuging in a cooled centrifuge 12. Liquid phases from the filter 10 and centrifuge 12 may be recycled to recover additional phenylalanine. The solid recovered from centrifugation is removed and placed in a dryer to yield the final product.

OTHER EMBODIMENTS

The liquid/solid separations effected by filtration in the above process also can be effected by centrifuging. The separations need not be part of a continuous flow process, but instead may be accomplished as discrete steps in a separation/purification. The complex may be dissociated by other means. For example, the pH may be lowered with another acid (e.g., H$_3$PO$_4$ for Ca$^{++}$) that forms a soluble salt with the metal ion and the amino acid is then crystallized by evaporation to increase its concentration. Alternatively, the ion can be removed using an ion exchange resin.

I claim:

1. A method of recovering phenylalanine from an aqueous mixture, said method comprising
   providing calcium salt in said mixture yielding Ca$^{++}$ ions in said mixture and
   maintaining the pH of said mixture between 8.5 and 11, thereby precipitating a complex comprising phenylalanine and Ca$^{++}$
   separating said precipitated complex from said aqueous mixture,
   dissolving said precipitated complex in an aqueous solution at pH below 8.5, and
   separating said phenylalanine from said Ca$^{++}$.

2. A method of recovering phenylalanine from an aqueous mixture comprising a solid phase and a liquid phase, said method comprising
   separating said solid and liquid phases,
   providing calcium salt yielding Ca$^{++}$ ions in said liquid phase and maintaining the pH of said liquid phase between 8.5 and 11, thereby precipitating a complex comprising phenylalanine and Ca$^{++}$
   separating said precipitated complex from said liquid phase,
   dissolving said precipitated complex in an aqueous solution at pH below 8.5, and
   separating said phenylalanine from said Ca$^{++}$.

3. The method of claim 2 wherein said aqueous mixture is a fermentation broth comprising microorganisms.

4. The method of claim 2 wherein said calcium salt is provided in said aqueous mixture.

5. The method of claim 2 wherein said calcium salt is added to said liquid phase after said solid and liquid phases are separated.

6. The method of claim 3 wherein said broth has a pH below 8.5 and said broth is separated into a solid phase and a liquid phase, after which the pH of the liquid phase is raised to between 8.5 and 11.

7. The method of claim 3 wherein portions of said fermentation broth are continuously drawn off from an operating fermentor.

8. The method of claim 3 wherein said solid phase is returned to said fermentation broth after said solid phase has been separated from said liquid phase.

9. The method of claim 7 or claim 8 wherein said liquid phase is returned to said fermenter after separation of said complex from said liquid phase.

10. The method of claim 3 wherein said fermentation broth is first separated into a solid and a liquid phase by filtration.

11. The method of claim 1 or 2 wherein said precipitated complex consists essentially of phenylalanine and calcium.

12. The method of claims 1 or 2 wherein said separated precipitated complex is dissolved in an aqueous solution comprising an acid that forms a soluble Ca$^{++}$ salt.

13. The method of claim 2 wherein said precipitated complex is separated from liquid phase by centrifugation.

* * * * *